(12) United States Patent
Inglis et al.

(10) Patent No.: US 11,871,904 B2
(45) Date of Patent: Jan. 16, 2024

(54) STEERABLE ENDOSCOPE SYSTEM WITH AUGMENTED VIEW

(71) Applicant: COVIDIEN AG, Neuhausen am Rheinfall (CH)

(72) Inventors: Peter Douglas Colin Inglis, Boulder, CO (US); Derek Scot Tata, Longmont, CO (US)

(73) Assignee: Covidien AG

( * ) Notice: Subject to any disclaimer, the term of this patent is extended or adjusted under 35 U.S.C. 154(b) by 129 days.

(21) Appl. No.: 17/089,258

(22) Filed: Nov. 4, 2020

(65) Prior Publication Data

US 2021/0137350 A1 May 13, 2021

Related U.S. Application Data

(60) Provisional application No. 62/951,512, filed on Dec. 20, 2019, provisional application No. 62/932,571, filed on Nov. 8, 2019.

(51) Int. Cl.
| | | |
|---|---|---|
| *A61B 1/005* | (2006.01) | |
| *A61B 34/10* | (2016.01) | |
| *A61B 1/00* | (2006.01) | |
| *A61B 90/50* | (2016.01) | |
| *A61B 1/05* | (2006.01) | |
| *A61B 90/00* | (2016.01) | |

(52) U.S. Cl.
CPC ......... *A61B 1/0051* (2013.01); *A61B 1/0005* (2013.01); *A61B 1/00006* (2013.01); *A61B 1/00016* (2013.01); *A61B 1/00018* (2013.01); *A61B 1/000095* (2022.02); *A61B 1/00194* (2022.02); *A61B 1/05* (2013.01); *A61B 34/10* (2016.02); *A61B 1/009* (2022.02); *A61B 2034/105* (2016.02); *A61B 2090/365* (2016.02); *A61B 2090/502* (2016.02)

(58) Field of Classification Search
CPC ............ A61B 1/00006; A61B 1/00016; A61B 1/00018; A61B 1/05; A61B 2034/105; A61B 2090/502
See application file for complete search history.

(56) References Cited

U.S. PATENT DOCUMENTS

| 6,503,195 B1 | 1/2003 | Keller et al. |
|---|---|---|
| 9,123,155 B2 | 9/2015 | Cunningham et al. |

(Continued)

FOREIGN PATENT DOCUMENTS

| WO | 2007106046 A2 | 9/2007 |
|---|---|---|
| WO | 2017066373 A1 | 4/2017 |

(Continued)

OTHER PUBLICATIONS

Lee, Hyung-Chul et al.; "Real-time endoscopic image orientation correction system using an accelerometer and gyrosensor," PLOS ONE, 12(11), Nov. 3, 2017, 12 pgs.

(Continued)

*Primary Examiner* — Aaron B Fairchild

(57) ABSTRACT

A steerable endoscope system is provided with an augmented view. An augmented reality display includes a rendered model of an anatomical structure corresponding to a patient anatomy pinned in the field of view, an endoscope marker moving through the virtual model, and an image from an endoscope at a location within the patient anatomy.

11 Claims, 11 Drawing Sheets

(56) References Cited

U.S. PATENT DOCUMENTS

| | | | |
|---|---|---|---|
| 9,767,608 B2* | 9/2017 | Lee | A61B 5/7445 |
| 10,010,379 B1 | 7/2018 | Gibby et al. | |
| 10,842,349 B2* | 11/2020 | Yamazaki | H04N 23/632 |
| 2006/0281971 A1 | 12/2006 | Sauer et al. | |
| 2007/0236514 A1 | 10/2007 | Agusanto et al. | |
| 2013/0267838 A1 | 10/2013 | Fronk et al. | |
| 2014/0275760 A1 | 9/2014 | Lee et al. | |
| 2016/0225192 A1 | 8/2016 | Jones et al. | |
| 2017/0128139 A1* | 5/2017 | Razzaque | A61B 18/1477 |
| 2018/0012413 A1* | 1/2018 | Jones | G06T 19/006 |
| 2018/0200018 A1* | 7/2018 | Silva | A61B 5/743 |
| 2018/0325499 A1* | 11/2018 | Landey | A61B 1/05 |
| 2019/0008595 A1* | 1/2019 | Popovic | A61B 34/20 |
| 2019/0231220 A1* | 8/2019 | Refai | A61B 1/00193 |
| 2020/0254204 A1 | 8/2020 | Moffat et al. | |
| 2020/0375666 A1* | 12/2020 | Murphy | G06T 19/003 |
| 2021/0128243 A1* | 5/2021 | Kumar | A61B 1/0005 |

FOREIGN PATENT DOCUMENTS

| | | |
|---|---|---|
| WO | 2022/133248 A1 | 6/2022 |
| WO | 2022/266500 A1 | 12/2022 |

OTHER PUBLICATIONS

International Search Report and Written Opinion for PCT Application No. PCT/EP2020/081179, dated Jan. 22, 2021, 14 pages.

* cited by examiner

STEERABLE ENDOSCOPE SYSTEM WITH AUGMENTED VIEW

CROSS-REFERENCE TO RELATED APPLICATIONS

The present disclosure claims priority to and the benefit of U.S. Provisional Application No. 62/932,571, filed on Nov. 8, 2019, and U.S. Provisional Application No. 62/951,512, filed Dec. 20, 2019, the disclosures of which are incorporated by reference in their entirety herein.

BACKGROUND

The present disclosure relates generally to medical devices and, more particularly, to steerable endoscope systems with an augmented reality view, and related methods and systems.

Medical endoscopes are long, flexible instruments that can be introduced into a cavity of a patient during a medical procedure in a variety of situations to facilitate visualization and/or medical procedures within the cavity. For example, one type of scope is an endoscope with a camera at its distal end. The endoscope can be inserted into a patient's mouth, throat, trachea, esophagus, or other cavity to help visualize anatomical structures, or to facilitate procedures such as biopsies or ablations. The endoscope may include a steerable distal tip that can be actively controlled to bend or turn the distal tip in a desired direction, to obtain a desired view or to navigate through anatomy.

During a medical or clinical procedure, one person may operate the endoscope (such as advancing it forward or backward into the patient cavity, steering the distal tip, and observing the camera image on a screen), while other individuals who are members of the medical or clinical team observe or assist. It can be difficult for these individuals to view the camera image from the endoscope, or maintain an accurate understanding of the position of the endoscope within the cavity as it is moved forward or backward.

SUMMARY

Certain embodiments commensurate in scope with the originally claimed subject matter are summarized below. These embodiments are not intended to limit the scope of the disclosure. Indeed, the present disclosure may encompass a variety of forms that may be similar to or different from the embodiments set forth below.

In an embodiment, a computer-controlled endoscope system is provided that includes an endoscope having a steerable distal tip with a camera producing an image signal and an orientation sensor producing an orientation signal. The system includes a first display having a hardware screen depicting images from the image signal and a second display having an augmented reality display. The augmented reality display includes a composite view of computer-generated graphics overlaid on a real-world field of view. The computer-generated graphics include an anatomical model pinned in the field of view, an endoscope marker positioned in the anatomical model according to the orientation signal and an illumination depicting a real-time direction of view of the camera.

In an embodiment, a graphical display is provided that includes a rendered model of an anatomical structure corresponding to a patient anatomy; an image from an endoscope at a location within the patient anatomy; and a graphical marker overlaid on the rendered model at a position corresponding to the location of the endoscope within the patient anatomy, wherein the graphical marker moves through the rendered model along with real-time movements of the endoscope within the patient anatomy.

In an embodiment, a computer-implemented method for generating an augmented reality display over a field of view is provided that includes the steps of receiving, at a controller, a position signal from an endoscope, the position signal comprising position, orientation, or movement data of a steerable distal end of the endoscope; receiving, at the controller, sensor signals from one or more sensors of the endoscope, the sensor signals comprising real-time data indicative of a patient anatomy; rendering, at the controller, virtual objects; and displaying the virtual objects through a head-mounted viewer. The virtual objects include a three-dimensional anatomical model registered to a real object in the field of view; and an endoscope marker positioned within the anatomical model at a current position of the endoscope.

Features in one aspect or embodiment may be applied as features in any other aspect or embodiment, in any appropriate combination. For example, features of a system, handle, controller, processor, scope, method, or component may be implemented in one or more other system, handle, controller, processor, scope, method, or component.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

A medical scope or endoscope as provided herein is a thin, elongated, flexible instrument that can be inserted into a body cavity for exploration, imaging, biopsy, or other clinical treatments, including catheters, narrow tubular instruments, or other types of scopes or probes. Endoscopes may be navigated into the body cavity (such as a patient's airway, gastrointestinal tract, oral or nasal cavity, or other cavities or openings) via advancement of the distal end to a desired position and, in certain embodiments, via active steering of the distal end of the endoscope. Endoscopes may be tubular in shape.

Advancement of long, flexible medical devices into patient cavities is typically via force transferred from a proximal portion of the device (outside of the patient cavity), that results in advancement of the distal tip within the patient cavity. As used herein, "proximal" refers to the direction out of the patient cavity, back toward the handle end of a device, and "distal" refers to the direction forward into the patient cavity, away from the doctor or caregiver, toward the probe or tip end of the device. For example, a doctor or other caregiver holding a proximal portion of the endoscope outside of the patient cavity pushes downward or forward, and the resulting motion is transferred to the distal tip of the endoscope, causing the tip to move forward (distally) within the cavity. Similarly, a pulling force applied by the caregiver at the proximal portion may result in retreat of the distal tip or movement in an opposing (proximal) direction out of the patient cavity. However, because patient cavities are not regularly shaped or sized, the endoscope moves through a tortuous path, and the transferred force in a pushing or pulling motion from the proximal end may not result in predictable motion at the distal tip.

It can be difficult for the doctor, or any caregiver in the room, to know where the endoscope is positioned within the patient anatomy, how far it has moved proximally or distally, and what path it has taken through the patient anatomy. This can be particularly difficult for caregivers, clinicians, doctors, nurses, or other staff in the room who are not directly operating the endoscope. These team members may not have a clear view of the endoscope screen, and may not be able to maintain a clear view of the endoscope as it moves forward (distally) into or backward (proximally) out of the patient. In addition, for certain clinical procedures that include coordinated actions of different caregivers, it is beneficial to provide real-time information about the progress of an endoscope and/or other tools used in the clinical procedure. Various embodiments of an augmented reality system are described below, for providing an augmented reality view of a patient and an endoscope during a clinical procedure.

Figure 1:
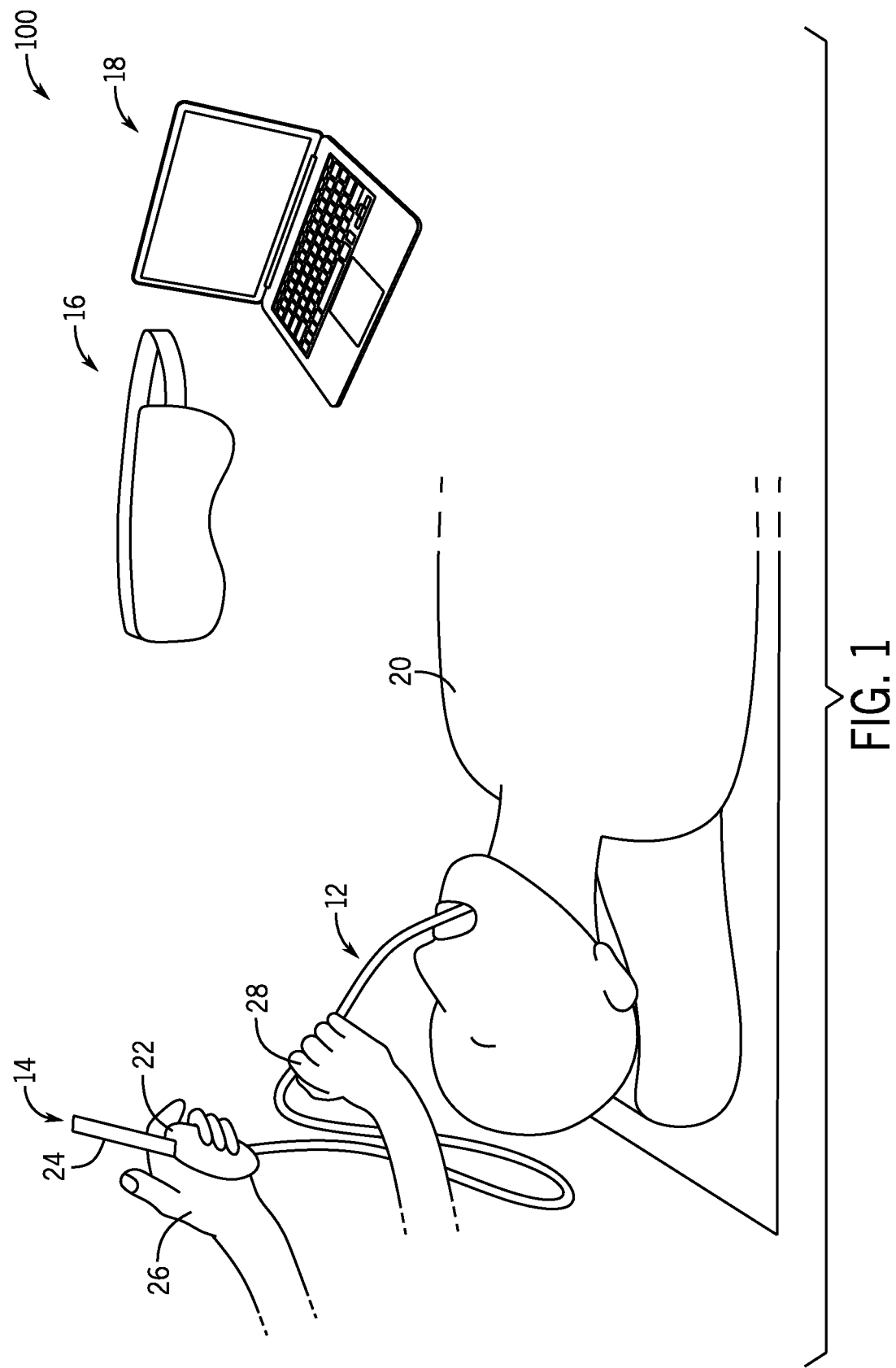
FIG. 1 is a view of an endoscope system, augmented reality viewer, and patient during a clinical procedure, according to an embodiment of the disclosure.

An example augmented reality (AR) system is used in conjunction with an endoscope viewing system 100 depicted in FIG. 1. In the embodiment shown, the endoscope viewing system 100 includes an endoscope 12 connected to an endoscope controller 14. The endoscope 12 is being inserted into a patient 20 during a clinical procedure. The system 100 also includes an augmented reality viewer 16, such as glasses, goggles, or a headset, connected wirelessly to an augmented reality controller 18, such as a laptop computer.

The view shown in FIG. 1 is the real-world view of the patient 20 and the clinical procedure without the augmented reality ("AR") view.

As shown in FIG. 1, the endoscope 12 is an elongated, tubular scope that is connected at its proximal end to the controller 14. The controller 14 includes a handle, puck, or wand 22 with a display screen 24. The display screen shows images from a camera at the distal end of the endoscope 12, within the patient cavity. The clinician who is operating the endoscope (the operator) holds the handle 22 with his or her left hand 26, and grips or pinches the endoscope 12 with his or her right hand 28. The operator can move the endoscope 12 proximally or distally with the right hand, while watching the resulting images from the camera on the display screen 24. In an embodiment, the display screen 24 is a touch screen, and the operator can input touch inputs on the screen 24 (such as with the operator's left thumb) to steer the distal tip of the endoscope, such as to bend it right, left, up, or down. In this example, the operator is using their right hand to move the endoscope forward into the patient's lungs, using their left thumb to steer the distal tip to navigate and adjust the camera's view, and watching the resulting camera view of the lungs (such as the bronchial tubes or passages) on the display screen 24. As described above, because proximal motion by the operator is not always translated directly to the distal tip inside patient anatomy, the operator may have difficulty knowing exactly where the distal tip is positioned inside the patient anatomy.

Additionally, as can be seen in FIG. 1, another clinician or caregiver in the room may have difficulty seeing the camera images on the display screen 24. In an embodiment, the display screen 24 is small and compact so that it can be battery-powered, lightweight, and hand-held by the operator holding the handle 22. The screen 24 may also be small so that the operator can keep a clear view of the patient 20 as well as the screen 24, in the same line of sight.

Embodiments are provided herein for an augmented reality view of the patient 20 during the clinical procedure. "Augmented reality" (AR) is computer-generated components, such as graphical images, super-imposed on the user's real-world field of view through the AR viewer 16, creating a composite view of both the real-world and computer-generated (virtual) objects. Augmented reality may also be referred to as "mixed reality." Augmented reality may include direct visualization of the real-world view through lenses (e.g., transparent or semi-transparent lenses) of the augmented reality viewer 16 or may include real-world captured image data along with computer-generated components displayed together on display surfaces of the augmented reality viewer 16. The AR system may include the AR viewer 16 and an AR controller 18 that communicates with and controls the display of virtual objects on the AR viewer 16.

Figure 2A:
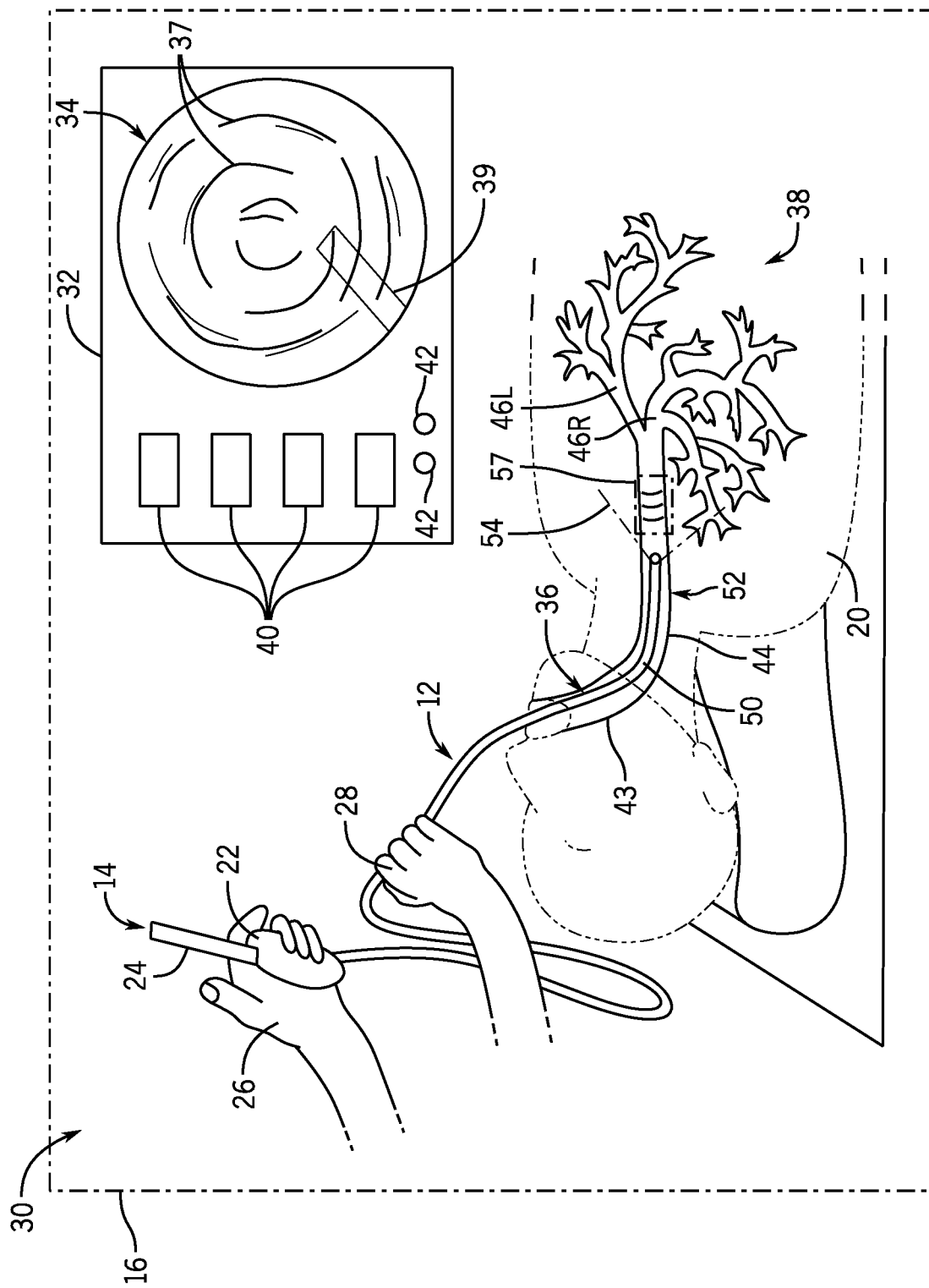
FIG. 2A is a view of the patient of FIG. 1, through an augmented reality field of view, according to an embodiment of the disclosure.

FIG. 2A is a view of the patient 20 of FIG. 1 through an AR field of view 30 as seen through the AR viewer 16. A user wearing the AR viewer 16 may be a supporting or assisting clinician or student who is not the endoscope operator. The augmented reality system permits visualization of the view through the endoscope 12 in the context of a computer-generated model of the patient's airway that is pinned to the patient. While the endoscope operator may generally remain close to the patient's mouth to navigate and manipulate the endoscope 12 within the airway, the user of the AR viewer 16 can move freely around the patient while maintaining the AR field of view 30. The AR field of view 30 superimposes computer-generated graphics on the real-world view of the patient 20 and the room. The computer-generated components can be visual (such as images and graphics), audible (such as noises, buzzers, and sounds), haptic (such as physical vibrations by the AR viewer 16 or other devices), or other interactions The AR view 30 can be achieved by a user putting on the AR viewer 16 (which may be implemented as headgear, such as the AR goggles shown in FIG. 1, or as glasses, other viewers, or screens including tablets and mobile devices) and activating the generation of the AR objects by the AR controller 18 (shown in FIG. 1). An embodiment of an AR view 30 is shown in FIG. 2A. In this embodiment, the AR view 30 includes the same real-world view of FIG. 1 (including, for example, the patient 20, endoscope 12, endoscope controller 14, and the operator's right and left hands 26, 28) as well as additional computer-generated graphics. These additional graphics augment the real-world view. The augmented graphics include a floating window 32, a three-dimensional anatomical model 38, and a simulated endoscope 36. Each of these graphics will be described in more detail below.

The floating window 32 is positioned toward the top of the AR view 30, leaving room for the patient 20 and anatomical model 38 below. The window 32 can be moved to another portion of the AR view 30 as desired by the user. The window 32 displays a camera image 34 that is the same camera image shown on the display screen 24. The camera image 34 is the image from the endoscope camera at the distal tip of the endoscope 12, inside the patient. In FIG. 2A, the camera image 34 is showing a view of the patient's trachea, including the patient's tracheal rings 37. In an embodiment, this image 34 is the current, real-time video feed from the camera at the distal end of the endoscope 12 during the clinical procedure and is the same as the image shown on the display screen 24 to the endoscope operator. As the patient condition changes and/or the endoscope steers or moves, the image 34 in the window 32 shows the current view from the endoscope camera. The camera image 34 shows anatomical features as well as any tools 39 (suctioning, biopsy, ablating, cutting, etc.) that are in field of view of the endoscope camera.

In an embodiment, the window 32 also includes data fields 40, displayed at the same time as the camera image 34. The data fields are shown to the left of the camera image 34, so that they do not block or overlap the camera image. In an embodiment, data fields, menus, buttons, and other display elements in the window 32 are sized and positioned so that the camera view 34 remains unobstructed during the clinical procedure. Different types of data can be displayed in the data fields 40. A few examples are patient vital signs, such as heart rate, $SpO_2$ (blood oxygen saturation), temperature, respiration rate, blood pressure, and others; a timer (counting up to show the total duration of time of the clinical procedure, total apneic time when the patient is not breathing spontaneously, or some other duration of time, or counting down to a particular time or milestone); battery life of a component in the system, such as the AR goggles 16, the endoscope controller 14, or other devices; patient data such as name, gender, weight, or identifying data; clinical data such as the type of procedure being performed; system status information, menus, or controls; and other suitable information. An individual team member can activate the AR viewer 16 and access this type of information without interrupting the clinical procedure ongoing in the room. When an emergency situation occurs (such as a prolonged apnea in the patient), caregivers in the room can quickly see relevant information (such as total apneic time) without interrupting their view of the patient.

In an embodiment, the window 32 also includes graphical buttons 42 that the user can push or click (such as with a pointer or gesture within the AR field of view 30) to change system settings. For example, the user may click a button 42 to toggle between different data in the data fields 40, or turn on or off different computer-generated displays. In an embodiment, graphical layers can be added to or removed from the AR field 30, as desired. An example graphical layer is a pulsing layer that pulses the model 38 (or the endoscope 36, or the window 32) in synchrony with the patient's heart rate. This layer can be activated if desired, or turned off if not desired. The user may click a button 42 to remove, add, or change portions of the anatomical model 38 or simulated endoscope 36, or activate or de-activate haptic feedback or image pulsing. For example, different structures of the anatomy (soft tissue, skeletal structures, or others) can be toggled on or off within the AR model 38.

In an embodiment, the user may click a button 42 to toggle between different camera views, if available. In an embodiment, a first camera view is a view from a laryngoscope camera, and a second camera view is a view from an endoscope camera, and the user may toggle between these two different views, or view them both at the same time in the window 32, or view them both at the same time as picture-in-picture views in the window 32. In an embodiment, the laryngoscope camera image is shown inside an outline of a first shape (such as a square or rectangular outline) and the endoscope camera image is shown inside an outline of a second different shape (such as an oval or circular outline as shown in image 34 in FIGS. 2-5).

In an embodiment, the user may click a button 42 to request a consult, page another caregiver, declare an emergency, send an alert, or request other assistance. The AR view can thus facilitate quick communication among a distributed team.

The computer-generated objects in the AR field of view 30 also include the three-dimensional anatomical model 38. In the embodiment shown in FIG. 2A, the model 38 is a model of the patient's airway, from the throat to the lungs. The model 38 is a computer-generated graphic object that includes the patient's throat 43 (or oral or nasal passages), trachea 44, right bronchial tube 46R, left bronchial tube 46L, and lower airway branches or bronchi 48. This three-dimensional model 38 is a computer-generated graphic that is overlaid on top of the real-world view of the patient 20. The model 38 may be shown in a transparent shade so that the patient 20 is visible through and behind the model 38.

The anatomical model 38 can be created in various different ways, such as using previously acquired image or anatomical data from the patient. In an embodiment, the model 38 is created from a scan of the patient 20 prior to the clinical procedure shown in FIGS. 2-5. The scan can be CT (computed tomography), MRI (magnetic resonance imaging), x-ray, or other diagnostic or imaging scans. These scans can be used to build a three-dimensional model of the actual anatomy of an individual patient. For example, computations from a CT scan can be used to build a three-dimensional model of a patient's airways (for example, computer-based methods for segmentation of anatomy based on CT scans). The resulting three-dimensional model shows the actual airway branches of that individual patient, as the airways split and branch out below the left and right bronchial tubes. In FIG. 2A, the anatomy of the model 38 is the patient's airways, but it should be understood that other anatomical models can be used in other procedures and contexts, including for example models of the skeleton, soft tissue, gastrointestinal structures, or others. The anatomical model 38 can be a simplified model generated from rich image data. That is, the overall anatomical model can be a cartoon view or smoothed version of the airways. The anatomical model 38 can be rendered to show the approximate locations and dimensions of airway passages and surrounding tissue walls, such as the tracheal or bronchial walls. For example, using CT scan data including density information, the anatomical model 38 can be generated based on density rules to designate less dense areas as likely to be open airway passages and more dense areas as likely to be tissue. Airway walls of the anatomical model are rendered based on tissue areas located at the border of open airway passages. In such an example, the tissue walls can be designated in the anatomical model 38 with or without fine feature resolution or texturing. The anatomical model 38 can be generated by or accessed by the AR system as provided herein.

In an embodiment, the anatomical model 38 is a generic or standard model of an anatomy, and is not specific to the patient 20. The model 38 is a default or pre-stored model that is used for generic indications of movement of the endoscope within the anatomy, such as a three-dimensional model of an adult trachea and lungs, or a pediatric trachea and lungs, or other anatomies. This generic model can be used for training purposes, or even during a procedure on a real patient, to give AR viewers some idea of the direction of movement and view of the endoscope within the patient 20, even if the model 38 is not built from the individual patient 20. The appropriate generic anatomical model for a patient can be used if a patient-specific anatomical model 38 is not available and can be selected or generated based on the patient's age, size, weight, and/or clinical condition.

The anatomical model 38 is built from data (whether patient-specific or generic) obtained prior to the clinical procedure. The model 38 is a static, global map of the anatomy. During the clinical procedure, the endoscope (or other instruments) will move within local areas of this global map, and will take live data (such as position and image data) from those areas. The AR field 30 combines the static, global map 38 with the live, real-time data from the distal tip of the endoscope, to show both the real-time location of the endoscope within that map, as well as the real-time local condition at that location (such as with live images or other data from the endoscope). Thus, the system combines the global map (such as previously collected 3D data) with the local surroundings (such as live 2D images and position data) to give a mixed view of the clinical procedure and patient condition, as further explained below.

In an embodiment, the anatomical model 38 is registered with the patient 20 in the AR field of view 30. This means that the AR system orients the model 38 with the patient 20, and maintains that orientation even as the AR user walks or moves around the room. The model 38 is "pinned" or pegged to the patient 20, so that the AR user can walk around the patient and view the model 38 from any point of view. Registration of a virtual component (such as the anatomical model 38) with a real-world object (such as the patient 20) can be accomplished with object recognition software, which can match the model and the patient through optical flow, feature detection, edge detection, fiducial markers, other image processing techniques. Three-dimensional mapping technologies, such as stereo cameras and LIDAR, can be used to map anatomical space and correlate key points between an imaging scan and reality.

In an embodiment, the AR visualization is anchored to the patient and does not rely on hardware that is externally fixed or installed in the operating room (OR) or other hospital setting. As such, the AR system operates in a plug-and-play manner to be used in conjunction with an available compatible endoscope 12 and endoscope controller. Patient anchoring provides a local or relative reference frame that moves with the patient, rather than a relatively more universal/stationary reference frame anchored in space in the OR or other facility. The distal endoscope camera within the patient is also not anchored (mechanically or virtually) to any stationary point in the room. Accordingly, the system can reduce or avoid misalignment between a live view of the patient and the 2D and 3D images. For example, if the patient moves within the room, the 3D model, the AR view, and all of the captured images move with the patient, and thus all the views stay aligned. The 3D model 38 is "pinned" (or "registered") to the patient in the room, and from there the 3D model 38 can stretch, twist, and move with the patient. Even though the 3D model 38 is pre-captured (and so the model itself is static), the model 38 can be stretched, rotated, or twisted as the patient breathes, coughs, rolls over, sits up, or moves.

In an embodiment, the model 38 is anchored or pinned relative to one or more detectable exterior patient features resolvable by a camera, such as a detected nasal opening, lips, or shoulder of the patient. In one example, camera-detectable codes (e.g., QR codes) or fiducial markers can be applied to the patient and used as anchor points to pin the model 38. By pinning the model 38 to the patient, the model 38 is anchored to the patient even during patient movement. If the patient moves (such as movements associated with coughing or jostling of the patient, or during patient transport between areas of a hospital), the AR system detects corresponding movement of the detectable features, and keeps the AR model 38 pinned to those features and thus to the patient. In this manner, the AR system is portable with the patient and is not tied to a particular room, environment, or external hardware.

Figure 2B:
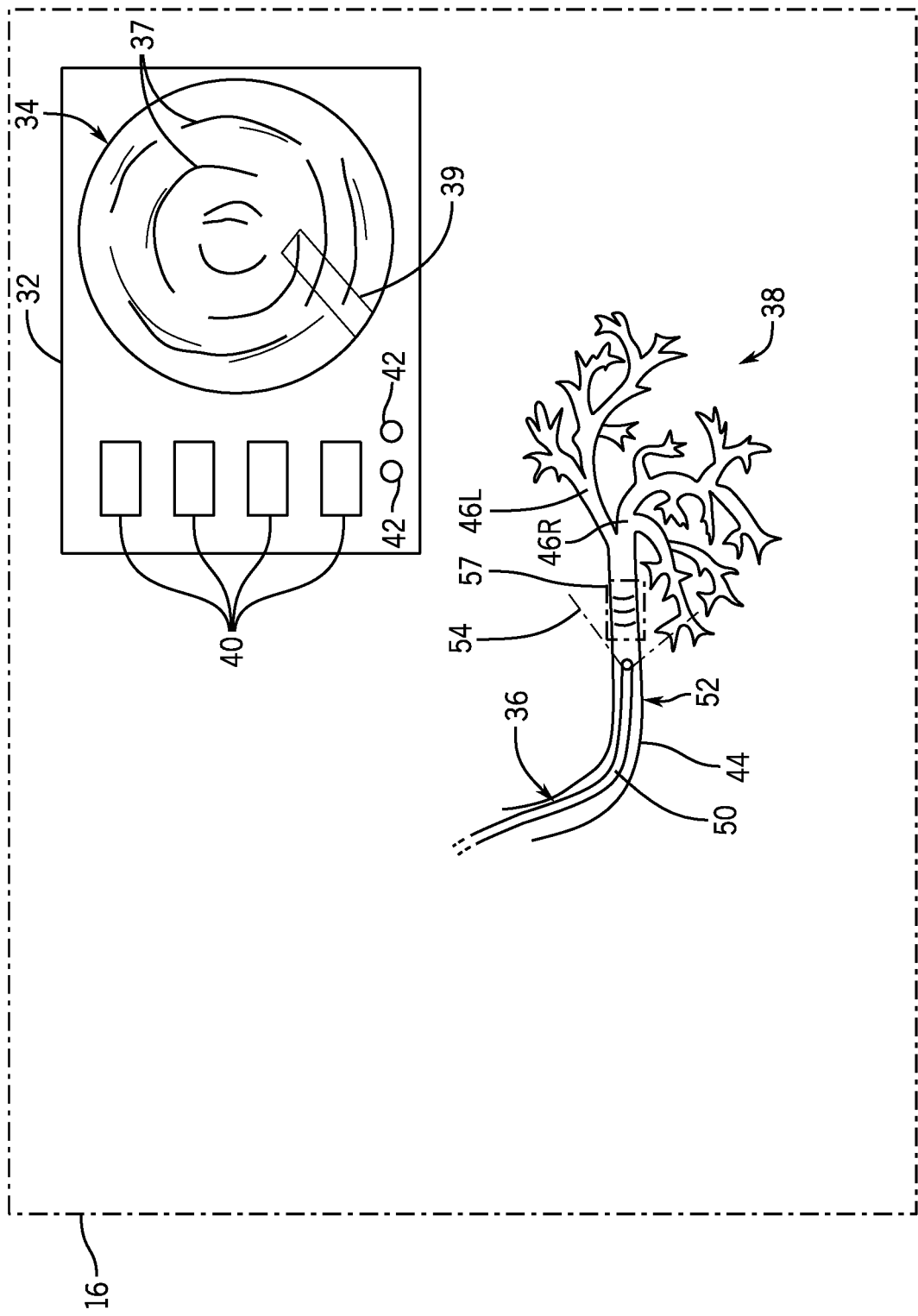
FIG. 2B is an augmented reality field of view of internal anatomy during a clinical procedure that is untethered to a real-time view of a patient, according to an embodiment of the disclosure.

Pinning the model 38 to the patient is possible but is not required to utilize the AR view. FIG. 2B shows an embodiment in which the anatomical model 38 as seen in the AR field of view 30 is untethered to the real-time view of the patient 20. Thus, the anatomical model 38 may be viewed by users whose AR field of view 30 does not include the patient 20 in certain embodiments. This may be beneficial for users whose view of the patient 20 is blocked by devices or other caregivers over the course of a medical procedure, or for users in a different room. In certain types of clinical procedures, it may be useful to view the model 38 separately from the patient 20, such as to keep a clear view of the patient separately from the AR field, or to view the AR field above a surgical drape, for example. In this case, the model 38 may be pinned to a different object in the room, or may be pinned to the patient but positioned above the patient, rather than overlaid on top of the patient's chest. Thus, the system may pin the model 38 to the patient or to another object in the room, or the model 38 may remain un-pinned, and the pinned or un-pinned model may be positioned on the patient, above the patient, or elsewhere.

In an embodiment, the floating window 32 is not registered with the patient 20, or with any real-world object in the field of view, and instead the window 32 remains in the upper right quadrant of the field of view 30 and remains facing the user, even as the user moves around the room. The floating window 32 may be deactivated by the user in certain embodiments.

The computer-generated graphics in the AR field of view 30 also include the simulated endoscope 36, as shown in FIGS. 2A and 2B. The simulated endoscope 36 is a computer-generated animation that represents the actual endoscope 12 that is being moved within the patient 20. The simulated endoscope 36 includes a tubular body 50, distal tip 52, and camera frustum 54. The camera frustum 54 is a conical section in front of the distal tip 52, and it represents the current direction of view of the camera on the real-world endoscope 12. That is, the dashed lines of the camera frustum 54 indicate the current orientation of the distal tip of the endoscope 12, to show the direction that the endoscope camera is pointed within the patient's anatomy.

The AR system renders the simulated endoscope 36 within the anatomical model 38, and moves the simulated endoscope 36 within the model 38 in coordination with movements of the real-world endoscope 12. The position of the simulated endoscope 36 within the model 38, and the orientation of the camera frustum 54, represent the actual position and orientation of the real-world endoscope 12 within the patient 20. Thus, when the endoscope operator advances the endoscope 12 distally within the patient, the AR system updates the rendering of the simulated endoscope 36 to move it a corresponding distance through the model 38. As the endoscope 12 is advanced, retracted, and steered throughout a clinical procedure, the AR system renders corresponding movements with the simulated endoscope 36 displayed in the AR field of view 30. As a result, the AR user (wearing the AR viewer such as the goggles 16) is able to more easily keep track of the position and orientation of the endoscope 12 in the patient 20. The simulated endoscope 36 is the marker showing the live, real-time, moving position of the endoscope within the global map of the model 38. The AR view shows the changing, current position of the endoscope in the model 38 similar to navigation of a vehicle through a street map.

In an embodiment, the model 38 and simulated endoscope 36 are shown on a flat display screen, rather than as an AR display overlaid onto a real-world field of view. For example, the view in FIG. 2B can be displayed on a display screen (such as a tablet, mobile device, laptop, or other display) to show the real-time location of the endoscope within the modeled patient anatomy.

As generally discussed, the model 38 is pre-rendered or generated in advance of endoscope insertion and is displayed in the AR view 30 as a virtual object. The location of the simulated endoscope 36 and the camera frustum 54 update within the AR view 30 in real-time according to real-time orientation data of the endoscope 12. The combination of the previously generated 3D model 38 and the real-time endoscope 36, frustum 54, a window 32 creates a mixed of previously acquired and live views.

Further, in an embodiment, the live 2D image data from the endoscope is added to the 3D model 38 in real-time to create a mixed view. In one example, the camera live feed is mapped or projected onto the anatomical model 38, as shown for example in FIG. 2A. The endoscope camera provides a real-time two-dimensional (2D) camera image 34 of the airway, and the image 34 is oriented in the real-world orientation of the endoscope camera. This 2D camera image 34 is projected or mapped into three dimensional (3D) space in the anatomical model so that the AR user can view the image data of the camera image 34 within the context of the 3D model. When the live 2D camera image is projected into the 3D model, the AR user can see the image data from the camera's point of view (such as anatomical and surgical features in front of the endoscope camera) while the user is looking at the 3D model in the AR view. This 2D image projection creates a mix of live, 2D image data with pre-acquired 3D model data, together in the AR view. This mix of data is shown in FIG. 2A, where the tracheal rings 37 from the 2D image 34 are projected onto the 3D model 38 within the camera frustum 54 (inside box 57).

The mapping or projection of the 2D image onto the 3D model can be performed by one or more components of the system 100 (FIG. 1), such as the AR controller 18. In one example, the mapping is accomplished by projecting the 2D image onto a 3D shape such as a tube, cone, partial cone, wall, or other shape. This shape may be determined from the anatomical model 38 or the data on which the anatomical model 38 is based, e.g., passage dimension information. In an embodiment, the mapping renders 3D displacements of the 2D image along the axis of the airway passage.

In an embodiment, to project the 2D camera view onto the 3D model 38, position data (gyroscope/accelerometer) is used to locate the endoscope distal tip relative to the model 38 and track a presence and degree of forward/backward movement of the distal tip. As the endoscope moves through the patient, the virtual endoscope 36 moves through the model 38. The 2D image is projected onto a portion of the 3D model in front of the distal tip (within the frustum 54). For example, in FIG. 2A, this portion is shown within highlighted box 57. The portion of the 3D model within this box 57 corresponds to the current, real-world captured view in the camera image 34. The floating window 32 presents the camera image 34 from the orientation or perspective of the endoscope camera, which is generally pointed along the axis of the airway. By contrast, the 3D mapping of the camera image 34 transforms or shifts the same image data into a different orientation—the orientation of the user, which may be orthogonal to the axis of the airway. When this 3D mapping is active, the floating window 32 can remain displayed or can be removed so that it is not displayed.

Figure 2C:
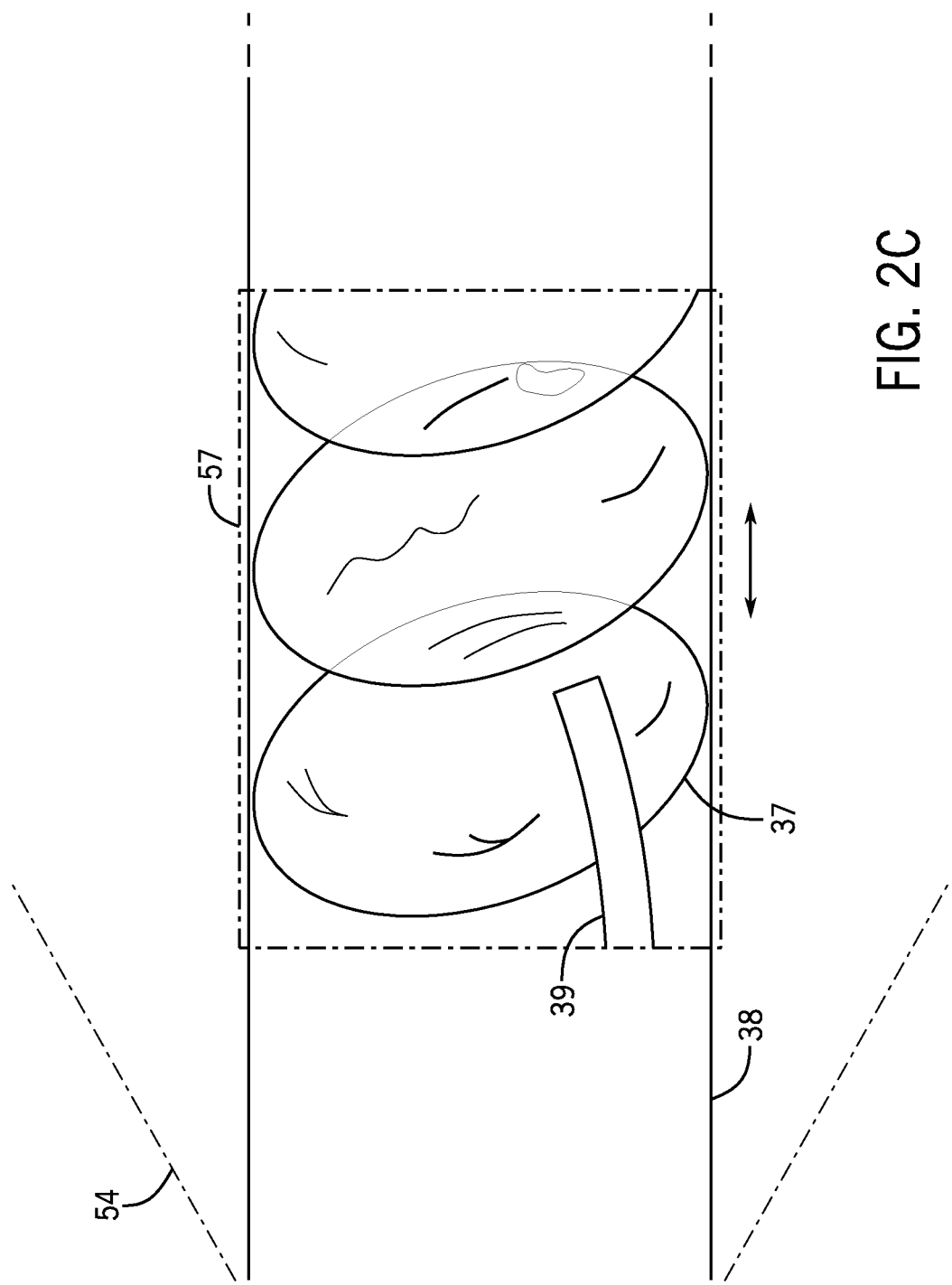
FIG. 2C is a detail view of an augmented reality field of view, according to an embodiment of the disclosure.

In an embodiment, the camera image 34 undergoes optical image processing that includes landmark recognition. Landmark recognition may involve identifying features that are present in the camera image 34 such as the vocal cords, bifurcations of passageways, or other anatomy landmarks, and/or identifying that the endoscope 12 moved past these features. Certain landmarks may be rendered in the 3D model, and the identification of the landmark in the image 34 can be correlated to the real-time tracking of the endoscope through the model, such as identifying an object in view—a polyp, blood vessel, etc.—and tracking the object as it moves by. Tracking may include pixel processing (assessment of changes of size of an object in the image to track endoscope movement). Another example includes identifying a bifurcation of branches and tracking that the endoscope moves into a branch, Mapping the 2D camera image 34 in real-time onto the 3D model may include texturing the corresponding portion of the anatomical model 38, shown in the highlighted box 57, that corresponds to the camera frustum 54. As the endoscope 12 moves within the airway, the highlighted box 57 that includes the texturing moves along with the simulated endoscope 36. As shown in FIG. 2C, the texturing incorporates features of the camera image 34, such as the tracheal rings 37, as well as any tools 39 present in the camera image 34, mapped onto the surface of the airway. The view of the tool 39 mapped into the 3-dimensional orientation provides additional clinical information during procedures. For example, the view of the tool 39 provides information as to a progress of a clinical procedure involving the tool and interactions between tools and tissue (grasping, jaws open, closed, tissue grabbed, suction performed, etc), which allows the caregivers to manage the patient's real-time condition and coordinate subsequent steps that are initiated based on the tool's actions. Providing this information via the AR viewer 16 improves coordination of such procedures. The texture mapping may also resolve features in the camera image 34 such as lesions, polyps, or areas of bleeding, along the 3-dimensional space. The texture mapping may use shading, transparency, and/or color intensity to show interior curvature of the airway passage walls and to distinguish between a closer wall and a farther wall of the airway, from the point of view of the user.

As the video feed in the camera image 34 updates during navigation of the endoscope 12, the mapping may move to an updated portion of the anatomical model 38 corresponding to the updated position of the endoscope 12. The mapping, such as the mapping in highlighted box 57, and any texturing, moves with the detection of the updated endoscope position and with receiving of updated image data. Thus, the real-time data represents live local conditions around the endoscope distal tip. This data may, in an embodiment, be retained as part of a historical tracking of the progress of the endoscope 12.

In certain embodiments, the real-time data may be used to update or correct the anatomical model 38 where there is a deviation between the anatomical model 38 and the real-time data. The updating may be according to a rules-based system, where the anatomical model 38 is updated with real-time data that (i) shows a deviation of a sufficient degree to perform an update (such as a deviation of a certain threshold size, type, or other standard) and (ii) is determined to be reliable (such as by meeting quality criteria). In an embodiment, a deviation (between the real-time data and the model) may be sufficient to perform an update if it shows a structural discrepancy between the model and the patient's anatomy, such as an airway passage at a different location or different size. In one embodiment, the quality of the incoming real-time data may be assessed based on corroboration between different real-time sensors. If the incoming live data from different sensors matches (shows the same deviation), the model 38 may be updated. These sensors may be part of separate tools that are sensing or monitoring the patient, or may be coupled to the distal tip of the endoscope 12. For example, the sensing structures may include an ultrasound transducer, an optical sensor (e.g., visible spectrum, or penetrating IR), gyroscope, magnetometer, temperature sensor, a time of flight sensor, or others. In an example, a time of flight sensor generates a signal that includes a density point cloud. The density point cloud information is processed to estimate surface features of the passageway, such as contours, color variations, or other texture features. If these features corroborate or match information from the endoscope camera, then the features are used to update the anatomical model 38. In another example, ultrasound data is segmented or otherwise processed to resolve surface texture information that is used to update the anatomical model 38. The mapping may include error or pattern matching to identify closest match portions of the anatomical model 38 onto which the live data is mapped.

In an embodiment, areas of detected deviation between the anatomical model 38 and the real-time data may be highlighted or shaded on the anatomical model 38 as a notification to the user in the AR viewer 16. Further, certain types of detected deviations may be weighted differently according to the rules-based system. In an embodiment, real-time data associated with temporary conditions, such as discoloration or bleeding, is not used to update the anatomical model 38, while real-time data associated with structural differences (passage size, shape, or contours) is passed to a quality check step to assess if the data is sufficiently high quality to use to update the anatomical model 38.

Figure 3:
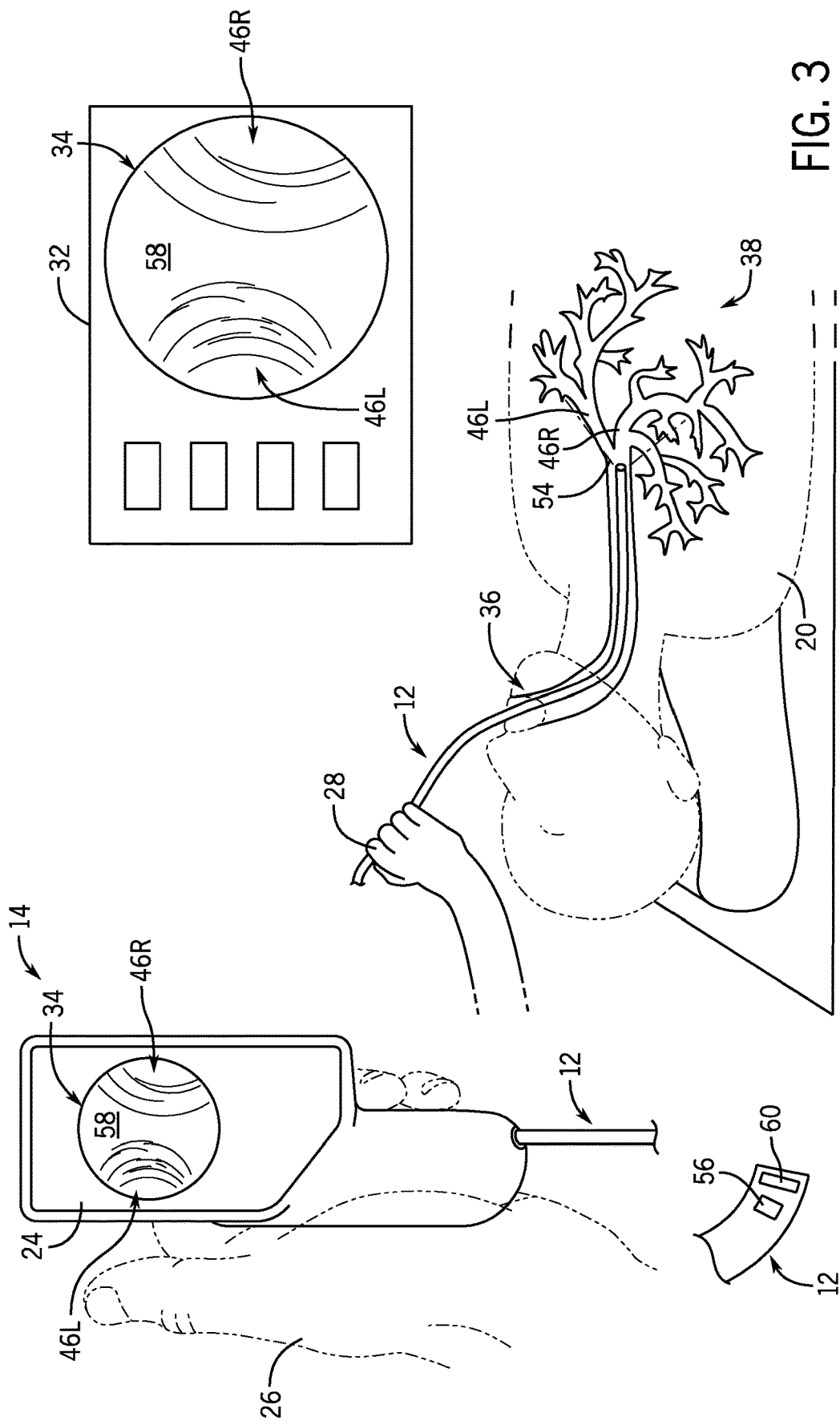
FIG. 3 is a view of the patient of FIG. 1, through an augmented reality field of view, and an inset view of an endoscope controller, according to an embodiment of the disclosure.

An example of simulated movement of the endoscope 12 in the AR view 30 is shown in FIGS. 2A and 3. In FIG. 3, the endoscope operator has advanced the endoscope 12 distally, with the operator's right hand 28, moving the endoscope 12 further forward into the patient airway, toward the carina 58. (The carina is the tissue at the end of the trachea, where the trachea divides into the left and right bronchial tubes 46L, 46R.) FIG. 3 shows a cut-away front view of the endoscope controller 14, showing the front of the display screen 24. The display screen 24 shows the same camera image 34 as is shown in the AR window 32. In this case, the image 34 shows the carina 58, left bronchial tube 46L, and right bronchial tube 46R. The same image 34 is shown on the endoscope display screen 24 (held by the endoscope operator), and the floating window 32 in the AR view 30. As a result, the AR viewer has the benefit of viewing the same clinical view as the endoscope operator, at the same time.

Additionally, in FIG. 3, the simulated endoscope 36 has moved forward distally within the anatomical model 38, toward the carina 58. The carina 58 and the left and right bronchial tubes 46L, 46R of the anatomical model 38 are now within the view of the camera frustum 54 of the simulated endoscope 36.

FIG. 3 also shows an enlarged cut-away view of the distal end of the endoscope 12. The endoscope 12 carries a camera 60 and an orientation sensor 56 at the distal tip of the endoscope. The camera 60 is positioned at the terminus of the distal end of the endoscope 12, to obtain a clear view forward. The orientation sensor 56 is located just behind the camera 60, so that position and orientation data from the sensor 56 is representative of the position and orientation of the camera 60. In an embodiment, the orientation sensor 56 is adjacent the camera 60. In an embodiment, the orientation sensor 56 is mounted on a flex circuit behind the camera 60. In an embodiment, the orientation sensor 56 is mounted on the same flex circuit as the camera 60, though the orientation sensor and the camera may or may not be in communication on the shared flex circuit. In an embodiment, the orientation sensor 56 has a size of between 1-2 mm in each dimension. In an embodiment, the camera 60 has a size of between 1-2 mm in each dimension.

Figure 4:
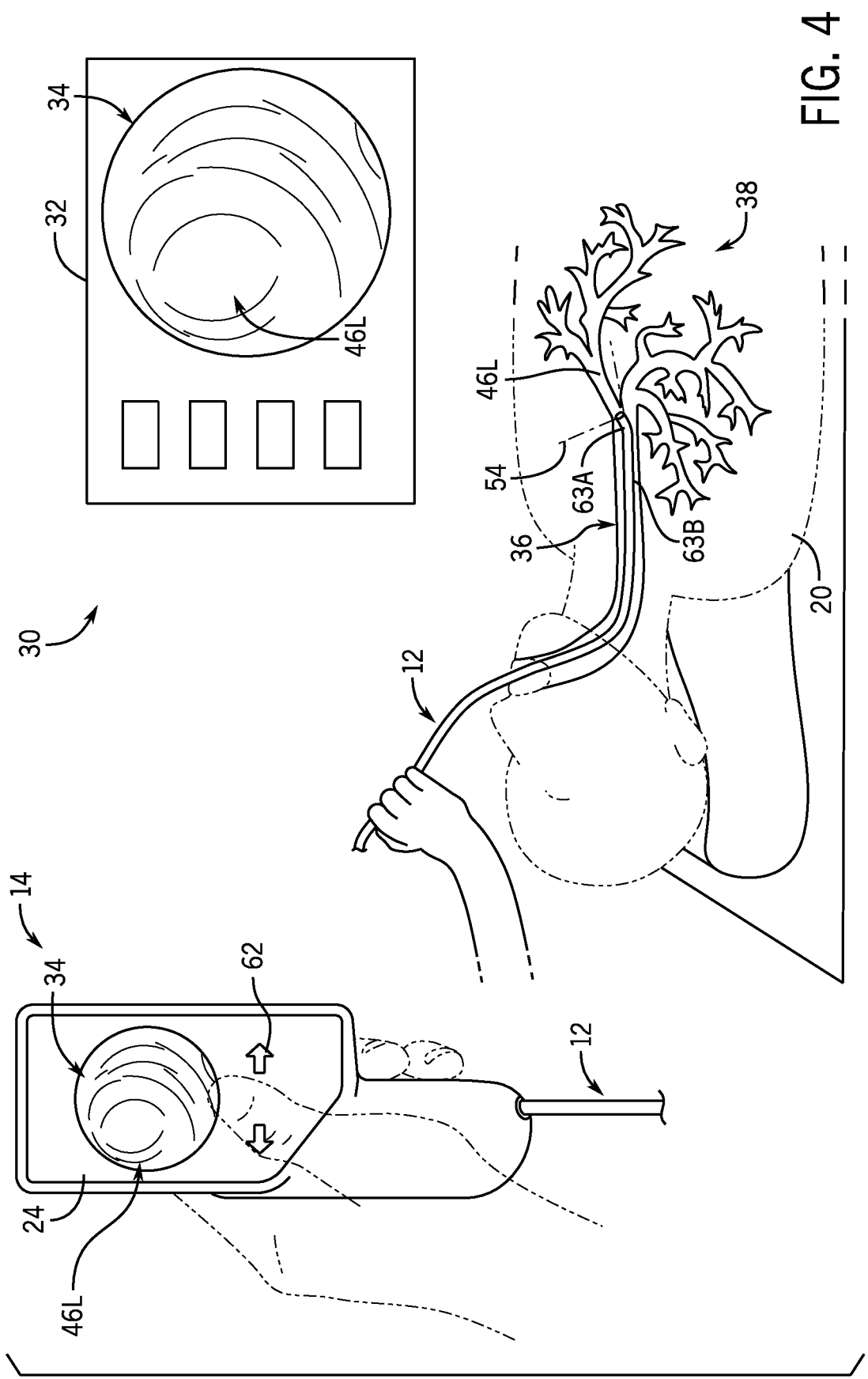
FIG. 4 is a view of the patient of FIG. 1, through an augmented reality field of view, and an inset view of an endoscope controller, according to an embodiment of the disclosure.

A steering movement of the endoscope 12 is shown in FIG. 4. In this example, the endoscope 12 has been steered to the patient's left, to visualize the left bronchial tube 46L. This real-world steering input is evidence by the view of the left bronchial tube 46L in the image 34 on the display screen 24. Additionally, the same camera image 34 is shown in the AR floating window 32. The AR system also simulates the steering direction of the endoscope 12, by rendering the simulated endoscope 36 with a turn to the left. As shown in FIG. 4, the camera frustum 54 is now pointed toward the left bronchial tube 46L. Thus the simulated endoscope 36 shows the actual steering movements and current orientation of the endoscope 12 inside the patient 20.

FIG. 4 also demonstrates that steering inputs from the endoscope operator on the endoscope controller 14 cause changes to the AR display 30. In FIG. 4, the endoscope operator enters a steering command on the endoscope controller 14, to bend or steer the distal tip of the endoscope 12. In the example shown, the steering command is a swipe input 62 on the display screen 24. The endoscope operator touches the display screen 24, which in this embodiment includes a touch screen interface, and swipes to the left or right (as indicated by the arrows 62), or up or down, to indicate which direction to bend or steer the distal tip of the endoscope 12. In another embodiment, steering commands may be received via other user inputs such as other touch inputs or gestures, softkeys on the display screen 24, hardware buttons or keys on the handle 22, or other inputs. The steering command entered by the endoscope operator to the endoscope controller 14 causes changes in both the real-world endoscope 12 and the computer-generated objects within the AR field of view 30. That is, the steering commands (such as swipe input 62) cause the endoscope 12 to bend or turn and also causes the simulated endoscope 36 within the AR field 30 to move, bend, or change position. In FIG. 4, the endoscope operator swipes his or her left thumb on the touch screen 24 to steer the endoscope 12 to the left. As a result the endoscope 12 bends to the left toward the patient's left bronchial tube 46L inside the patient, and the simulated endoscope 36 moves its camera frustum 54 toward the left bronchial tube 46L in the anatomical model 38. In this way, the computer-generated graphics augmenting the AR view 30 actively respond to touch inputs on the endoscope controller 14. In the example in which the camera frustum 54 defines an illuminated or highlighted portion of the model 38, the change in angle of the frustum 54 is reflected in altered illumination angles or highlighting rendered on the model 38.

Further, for endoscopes 12 that have independently addressable steerable segments (segments 63A, 63B), the endoscope marker 36 may indicate demarcations between the segments 63A, 63B and their relative positions and orientations to one another. Each segment 63A, 63B may have a separate orientation sensor that provides an orientation signal that is used to render the segments of the endoscope marker 36 and indicate the relative orientation of the segments 63A, 63B. In another example, the endoscope 12 may send the steering instructions to the AR controller, which estimates the orientation of the more proximal segment 63B based on an orientation signal from the more distal segment 63A and any steering instructions provided to the segments 63A, 63B.

Figure 5:
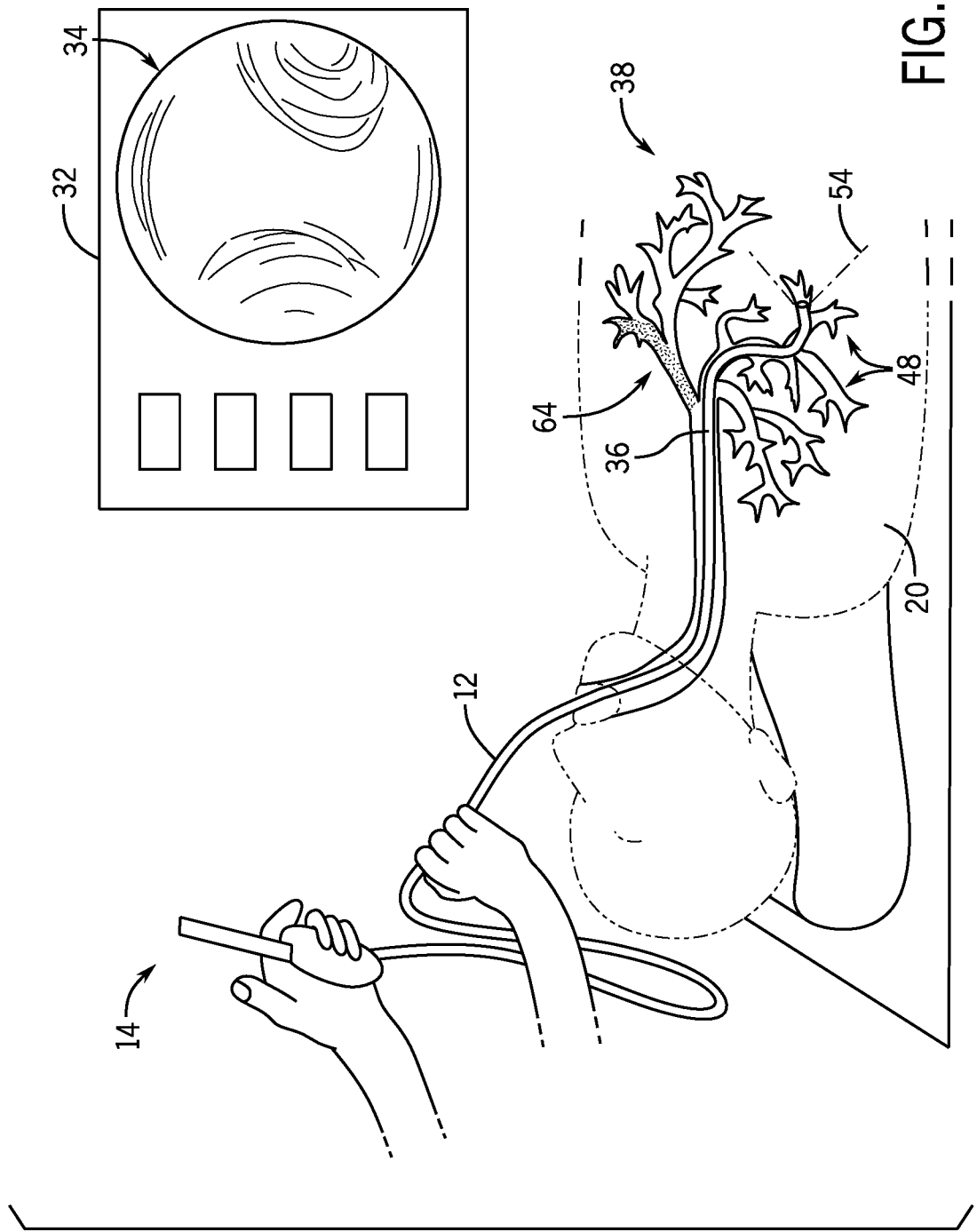
FIG. 5 is a view of the patient of FIG. 1, through an augmented reality field of view, according to an embodiment of the disclosure.

FIG. 5 shows an example where the endoscope 12 has traveled farther down the patient's airways, moving through the right bronchial tube and down into lower branches of the patient's bronchi 48. The simulated endoscope 36 shows this path and shows the current position of the endoscope within the patient's airways. Without the benefit of this augmented view, a clinician who is assisting the procedure in the room but not operating the endoscope may have difficulty understanding where the endoscope 12 is currently positioned within the patient 20. The AR view presents that real-time position information in a way that is easy to see and understand.

This computer-generated augmented-reality view can be useful in many different clinical scenarios. One example is training, where a student or less-experienced clinician wears the AR viewer 16 and watches a clinical procedure (on a patient or on a mannequin) through the AR view 30. With the AR objects in view, the student or trainee can better understand what is happening inside the patient during a real or simulated procedure. The AR system can also be used when the student or trainee is operating the endoscope 12, and the teacher or mentor or wearing the AR viewer 16 and watching the student's progress. The student and teacher can take turns wearing the AR viewer 16 and watching the procedure through the AR field, to practice and demonstrate different techniques and clinical procedures.

Another example is use by one or more trained clinical professionals during a clinical procedure, such as doctors, nurses, or assistants who are monitoring the progress of the procedure. The AR view 30 can enable these other team members to prepare or provide interventional tools or instruments at the right time, to monitor the patient's status, and/or to be ready to operate. Members of a surgical team can monitor intubation or scoping through the AR field 30 and be prepared to step in when needed to assist or operate on the patient. An anesthesiologist can monitor a procedure while managing anesthesia for the patient. A specific example is monitoring an awake intubation of a patient using the endoscope 12. An awake intubation can be challenging, and the AR view 30 permits the multiple team members of the procedure to be positioned around the patient while maintaining a view of endoscope's progress. In an embodiment, the AR system is viewed by multiple different users at the same time, and each of them may customize their view independently of each other (such as customizing the floating window 32).

The AR field 30 can utilize various highlighting, colors, grids, transparencies, windows, overlays, and other graphical components. In an embodiment, the camera frustum 54 is depicted as a computer-generated graphic in the anatomical model 38 and can be rendered as an illuminated area in a conical shape adjacent the distal tip of the simulated endoscope 36. The illumination can be modeled as light shining onto the three-dimensional anatomical model 38, so that the cone of the frustum 54 actually illuminates the anatomical features of the model 38 within its conical view. For example, the illumination is provided as a virtual object or as highlighting rendered on the anatomical model 38 according to a sensed position of the endoscope 12. In the example in which the model 38 is textured with anatomical features in the illuminated portion, the mapping may adjust brightness and darkness in the image data to indicate varying levels of illumination mapped farther away from the light source of the endoscope 12. Alternatively, the frustum 54 can be depicted as dashed lines spreading out from the distal tip of the simulated endoscope 36, or as a conical area of a particular color, with some transparency to enable the anatomical model 38 to be visible through the color. The cone can fade in intensity as it moves distally away from the distal end of the endoscope. Other combinations of color, lines, dashes, transparency, and illumination can be implemented within the AR field.

The simulation of the endoscope 36 can also take various shapes, colors, or forms. In an embodiment, the simulated endoscope 36 is shown with a long proximal tail, extending to the proximal end of the model 38, such as in FIG. 3. In another embodiment, the proximal tail of the endoscope is truncated, and instead only a small segment of the endoscope 36 is simulated, such as in FIG. 4. At its proximal end, the simulated endoscope 36 can be truncated or faded, so that it does not take up space in the AR field or unnecessarily block any view. As another example, the proximal end of the endoscope 36 may extend back past the carina 58 and stop or fade there, as shown in FIG. 5. Various other graphical representations, colors, and images can be used to render the simulated endoscope 36.

In an embodiment, the AR field shows a breadcrumbs path or trail showing the history of movement of the endoscope 36 in the model 38. An example is shown in FIG. 5, where the model 38 includes a shaded region 64. This shaded region 64 indicates that the endoscope 36 previously passed through that region of the model 38, before moving to its current position. In an embodiment, the model 38 includes three different types of shading or illumination—a first, brightest illumination within the frustum 54, showing the current view of the endoscope (such as a relatively brighter yellow, pink, orange, or other color illuminating the model 38); a second, less-bright illumination in the region 64 showing where the endoscope has previously traveled (such as the same color but relatively less bright); and the remainder of the model 38 which is least bright (such as a relatively more dim, transparent grey) than the other two regions, indicating that the endoscope has not traveled there.

In an embodiment, highlighting such as the shaded region 64 is used to show a desired path forward into the patient anatomy, rather than a history of past movements. The shading 64 or other visual cues can be placed within the model 38, serving as waypoints to indicate to a user a desired path for the endoscope into the patient cavity, such as highlighting the bronchi that lead to the target area for a clinical procedure. These waypoints can be toggled on or off during the procedure. A waypoint menu can be called (such as by clicking buttons 42) to select waypoints in the anatomy, or to view waypoints previously saved ahead of the procedure.

Figure 6:
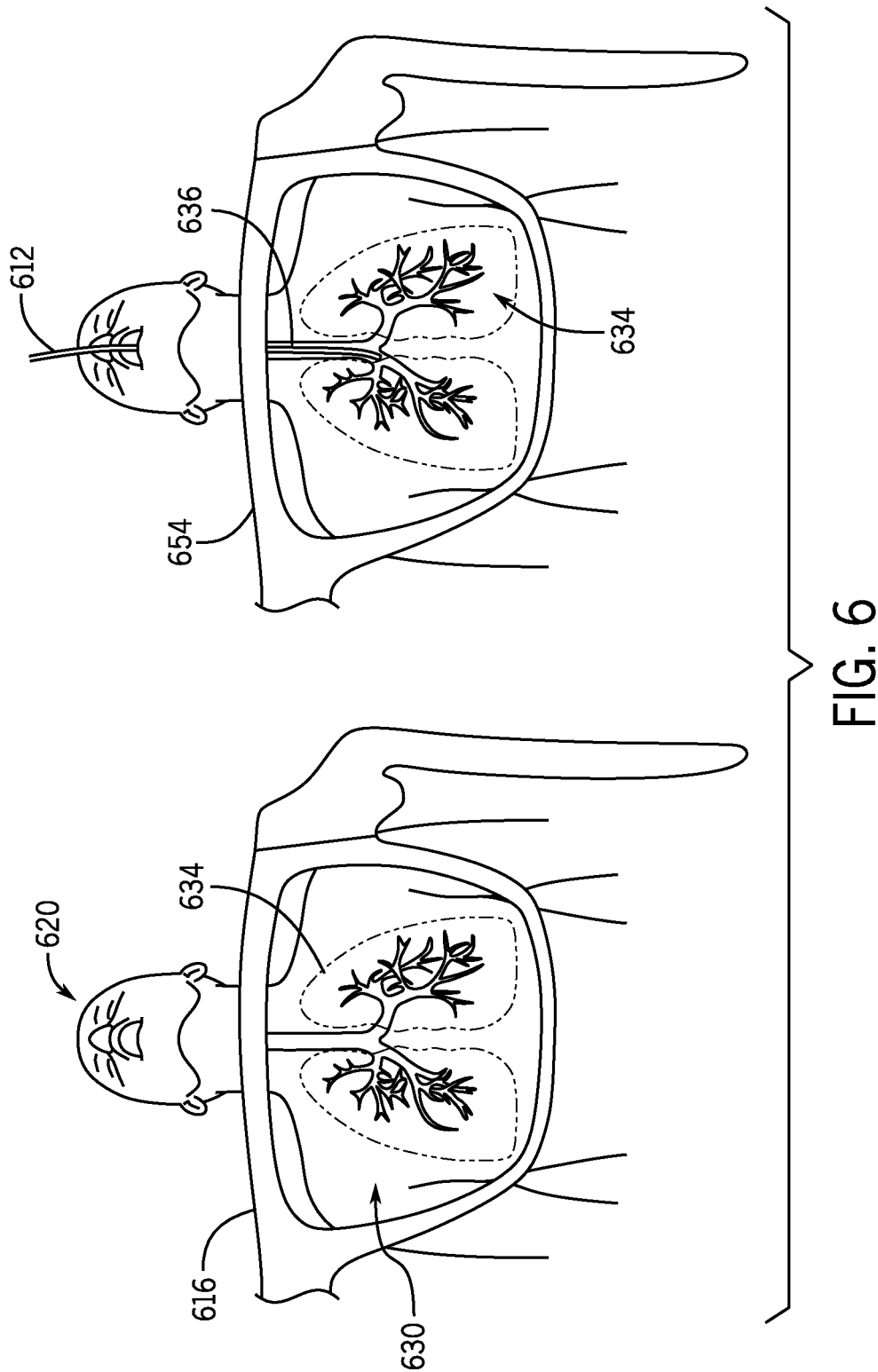
FIG. 6 is a cut-away view of augmented reality glasses providing an augmented reality view of a patient during a procedure with an endoscope, according to an embodiment of the disclosure.

FIG. 6 shows another representation of an AR system, according to an embodiment. In this example, an AR field 630 is visible through an AR viewer 616, in this case a pair of smart glasses. The AR field 630 augments the view of the patient 620 by superimposing an anatomical model 634 over the patient's chest. The anatomical model 634 includes computer-generated graphics of the patient's lower trachea and lungs. On the right side of FIG. 6, an endoscope 612 is introduced into the patient's airway, and the AR field 630 adds a simulated graphical endoscope 636. The distal tip of the simulated endoscope 636 indicates the current position of the endoscope 612 inside the patient 620. An area 654 of the anatomical model 634 is illuminated in front of the endoscope 636, to indicate the current view of the endoscope camera, in this case along a main branch of the patient's right bronchial tube.

Figure 7:
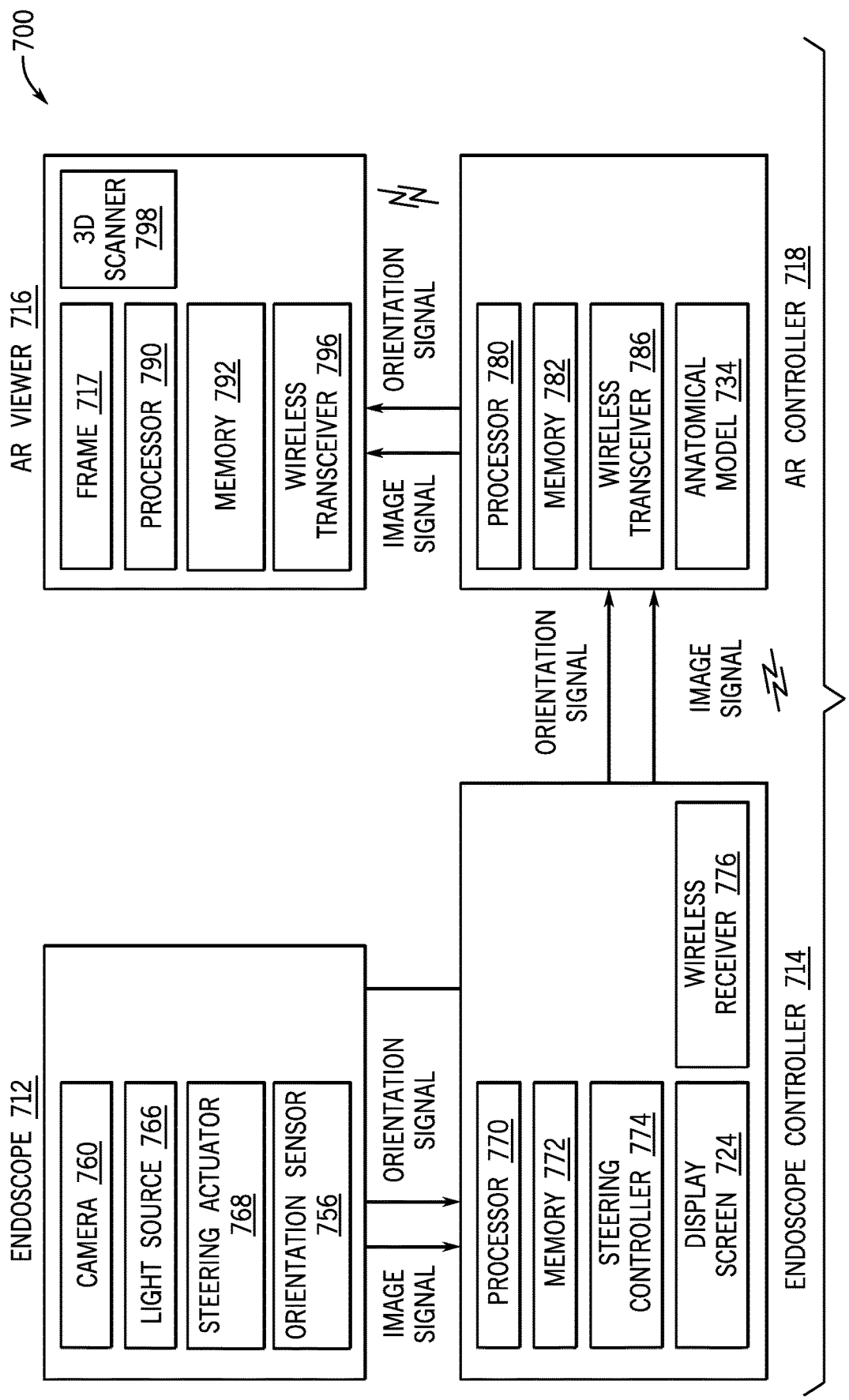
FIG. 7 is a schematic block diagram of an augmented reality endoscope system, according to an embodiment of the disclosure.

A block diagram of an augmented reality endoscope system 700 is shown in FIG. 7, according to an embodiment. As shown, the system includes an endoscope 712, endoscope controller 714, AR controller 718, and AR viewer 716. The endoscope 712 includes a camera 760, light source 766 (such as an LED shining forward from the distal tip of the endoscope), a steering actuator 768 (coupled to distal steerable segments of the endoscope, to bend or un-bend them as described below), and an orientation sensor 756. The endoscope 712 is connected by a wired (shown) or wireless connection to the endoscope controller 714, which includes a processor 770, hardware memory 772, steering controller 774 (such as a motor or other driver for operating the actuator 768), display screen 724, and wireless transceiver 776. The endoscope controller 714 is connected by a wired or wireless (shown) connection to the AR controller 718, which also includes a processor 780, hardware memory 782, wireless transceiver 786, and the stored anatomical model 734. The AR controller 718 may be, for example, a laptop or desktop computer running software stored on the memory 782. The AR controller 718 is connected by a wired or wireless (shown) connection to the AR viewer 716, which includes a viewing frame 717 (such as goggles or glasses), a processor 790, hardware memory 792, and a wireless transceiver 796. The AR viewer 716 also includes a front-facing 3D scanner 798 or camera that captures the field of view of the AR viewer. The data from the 3D scanner 798 or camera is communicated to the AR controller 718 as an input for pinning virtual objects (such as the 3D model 38) to real-world objects (such as the patient) within the AR field of view.

In an embodiment, the endoscope (such as endoscope 12, 612, 712) includes one, two, or more steerable segments at the distal end of the endoscope. Each steerable segment can articulate independently of the other segments. In an embodiment, each steerable segment can bend and curve in three dimensions (not just in a single plane, such as up/down or right/left), curving to points in all directions up to a limit of its range of motion. For example, in an embodiment each segment can bend up to 90 degrees in any direction, enabling it to move within a hemisphere having a radius equal to the segment's length. Each segment is manipulated by its own actuation system, including one or more actuators (such as sleeved pull-wires or other actuators described below), which moves to bend or un-bend the segment into or out of a curved or bent shape.

Each articulating segment at the distal end of the endoscope is manipulated by a steering system (such as steering controller 774), which operates an actuator (such as steering actuator 768) that is coupled to the segment to bend or straighten the segment. The steering system may include one or more memory metal components (e.g., memory wire, Nitinol wire) that changes shape based on electrical input, a piezoelectric actuators (such as the SQUIGGLE motor from New Scale Technologies, Victor N.Y.), a retractable sheath (retractable to release a pre-formed curved component such as spring steel which regains its curved shape when released from the sheath), mechanical control wires (pull wires), hydraulic actuators, servo motors, or other means for bending, rotating, or turning the distal end or components at the distal end of the endoscope.

In an embodiment, a graphical user interface (GUI) is presented on the display screen 724 of the endoscope controller 714. In an embodiment, the display screen 724 is a touch screen. The GUI receives user inputs by detecting the user's touch on the screen 724. The user touches the screen to indicate where the user wants to point the camera (such as camera 760 of endoscope 712). The GUI sends this touch input to a processor (described more fully below), which generates instructions to operate the steering system to bend one or more distal segments to point the camera axis in the direction that the user indicated.

In an embodiment, the display screen 724 includes a touch screen that is responsive to taps, touches, or proximity gestures from the user. For example, the user may enter a touch gesture (such as a tap, double-tap, tap-and-hold, slide, or swipe) to identify a target point or direction within the image on the screen. This gesture identifies where the user desires to steer the endoscope, and the controller translates this into a real-world steering direction and corresponding instructions for operating the steering system to move the distal steerable segment of the endoscope in that direction. The user may swipe in a desired direction on the touch screen 724 to reorient the distal end of the endoscope. A desired orientation or movement of the camera may be interpreted from the direction and length of the swipe movement on the touch screen 724. In an embodiment, the steering input may additionally or alternatively be provided via user selection from a menu, selection of soft keys, pressing of buttons, operating of a joystick, etc.

In an embodiment, the controller 714 together with the endoscope 712 operates as a two-part endoscope, where the controller 714 serves as the handle, display, and user input for the endoscope 712. In an embodiment, the controller 714 is reusable and the endoscope 712 is single-use and disposable, to prevent cross-contamination between patients or caregivers. The controller 714 itself does not need to come into contact with the patient, and it can be wiped and cleaned and ready to use for the next patient, with a new sterile endoscope 712. In an embodiment, the controller 714 is a hand-held wand, and the endoscope 712 is removably connected directly to the wand, for passage of control signals from the wand to the endoscope and video and position signals from the endoscope to the wand. In other embodiments the controller 714 may have other forms or structures, such as a video laryngoscope, table-top display screen, tablet, laptop, puck, or other form factor.

The endoscope controller 714 may be configured to detect coupling of a compatible endoscope 712 and the presence of in-range AR viewers 716 of the endoscope system 700 to activate communication between various components of the system 700. In this manner, the endoscope system controller 14 may operate in one mode as a traditional endoscope viewing device and, upon activation of a coupled AR viewer 16 and controller 718, may communicate camera and orientation information to the AR controller 718.

The block diagram of FIG. 7 shows the signal flow between the various devices. In an embodiment, the endoscope 712 sends an image signal (from the camera 760) and an orientation signal (from the orientation sensor 756) to the endoscope controller 714. The endoscope controller 714 receives the image signal and displays image data on the display screen 724. The endoscope controller 714 also forwards the image signal and the orientation signal to the AR controller 718, such as through the wireless transceivers on the two devices, and/or through wired connections and/or intermediary devices. The AR controller 718 receives the image signal and provides the image data in the flowing window 32 through the AR viewer 716. The image signal may also be routed to other devices, processor, or servers, and for example may be displayed or stored on other display screens, devices, or other AR views. In an embodiment, the AR viewer 716 is wireless, and can be operated untethered to other devices during use. In an embodiment, the AR viewer 716 is a wearable viewing device, such as a head-mounted display (an example is the HoloLens device from Microsoft).

The AR controller 718 receives the orientation signal and uses that information to update the rendering of the simulated endoscope in the anatomical model. The orientation sensor 756 is an electronic component that senses the orientation (such as orientation relative to gravity) and/or movement (acceleration) of the distal end of the endoscope. The orientation sensor 756 contains a sensor or a combination of sensors to accomplish this, such as accelerometers, magnetometers, and gyroscopes. The orientation sensor 756 may be an inertial measurement unit (IMU). The orientation sensor 756 detects static orientation and dynamic movement of the distal tip of the endoscope and provides a signal indicating a change in the endoscope's orientation and/or a motion of the endoscope. The orientation sensor 756 sends this signal to the controller 718. The orientation sensor 756 is located inside the tubular housing of the endoscope 712. As shown in FIG. 3, in an embodiment, the orientation sensor is located very close to the terminus of the distal end of the endoscope, such as behind the camera, to enable the orientation sensor 756 to capture much of the full range of movement of the distal tip and camera. In an embodiment, the orientation sensor 756 is placed at a distal end of the first steerable portion, remote from the proximal end of the steerable portion, to place the orientation sensor away from the fulcrum of movement.

In an embodiment, the orientation sensor 756 generates an orientation signal with position coordinates and heading of the distal tip of the endoscope 712, and sends the orientation signal to the endoscope controller 714. The endoscope controller 714 then sends the orientation signal to the AR system, such as to the AR controller 718, which uses this coordinate and heading information to update the position of the simulated endoscope within the anatomical model 734. For example, when the real-world endoscope 712 is moved distally by a distance of 1 mm inside the patient, this change in position is reported by the orientation sensor 756 through the orientation signal. The new position coordinates are received by the AR controller 718, and the simulated endoscope is moved forward (distally) by the same or proportional amount within the anatomical model 734. The new position is then rendered graphically in the display (such as floating window 32) through the AR viewer 716. The data signal from the orientation sensor 756 may be referred to as an orientation signal, movement signal, or position signal.

In an embodiment, the AR controller 718 uses both the orientation signal and the image signal to determine how to move the endoscope marker within the anatomical model 734. Image segmentation, object detection, object tracking, optical flow, and other computer vision techniques can be used to confirm or verify movement of the endoscope in a particular direction or by a particular amount. For example, referring to FIGS. 3-4, the AR controller can monitor the image signal to track movement of the endoscope toward and then into the left bronchial tube 46L.

Figure 8:
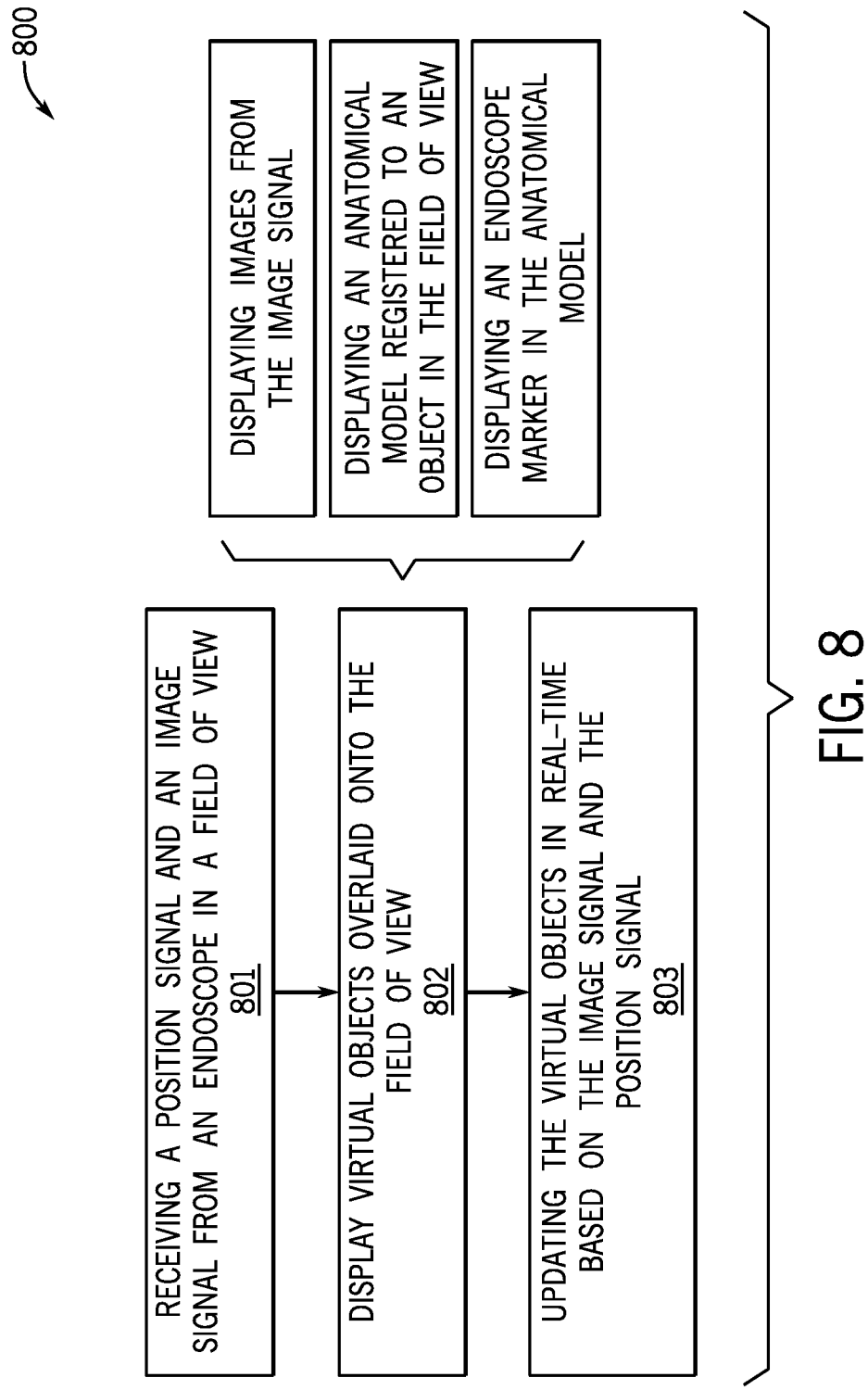
FIG. 8 is a flowchart of a method of providing an augmented reality view of a patient during a procedure with an endoscope, according to an embodiment of the disclosure.

FIG. 8 is a flowchart depicting a method 800 for providing an augmented reality view of a patient during a procedure with an endoscope, according to an embodiment of the disclosure. The method includes receiving a position signal and an image signal from an endoscope in a field of view, at 801. The position signal includes position, orientation, and/or movement data from the orientation sensor of the endoscope, and the image signal includes image data from the camera of the endoscope. The position signal and image signal are received at the AR controller. The method also includes displaying virtual objects overlaid onto the real-world field of view, at 802, including displaying images from the image signal, displaying a stored three-dimensional anatomical model registered to an object in the field of view, and displaying an endoscope marker in the anatomical model. The method also includes updating the virtual objects in real-time based on the image signal and the position signal, at 803.

Figure 9:
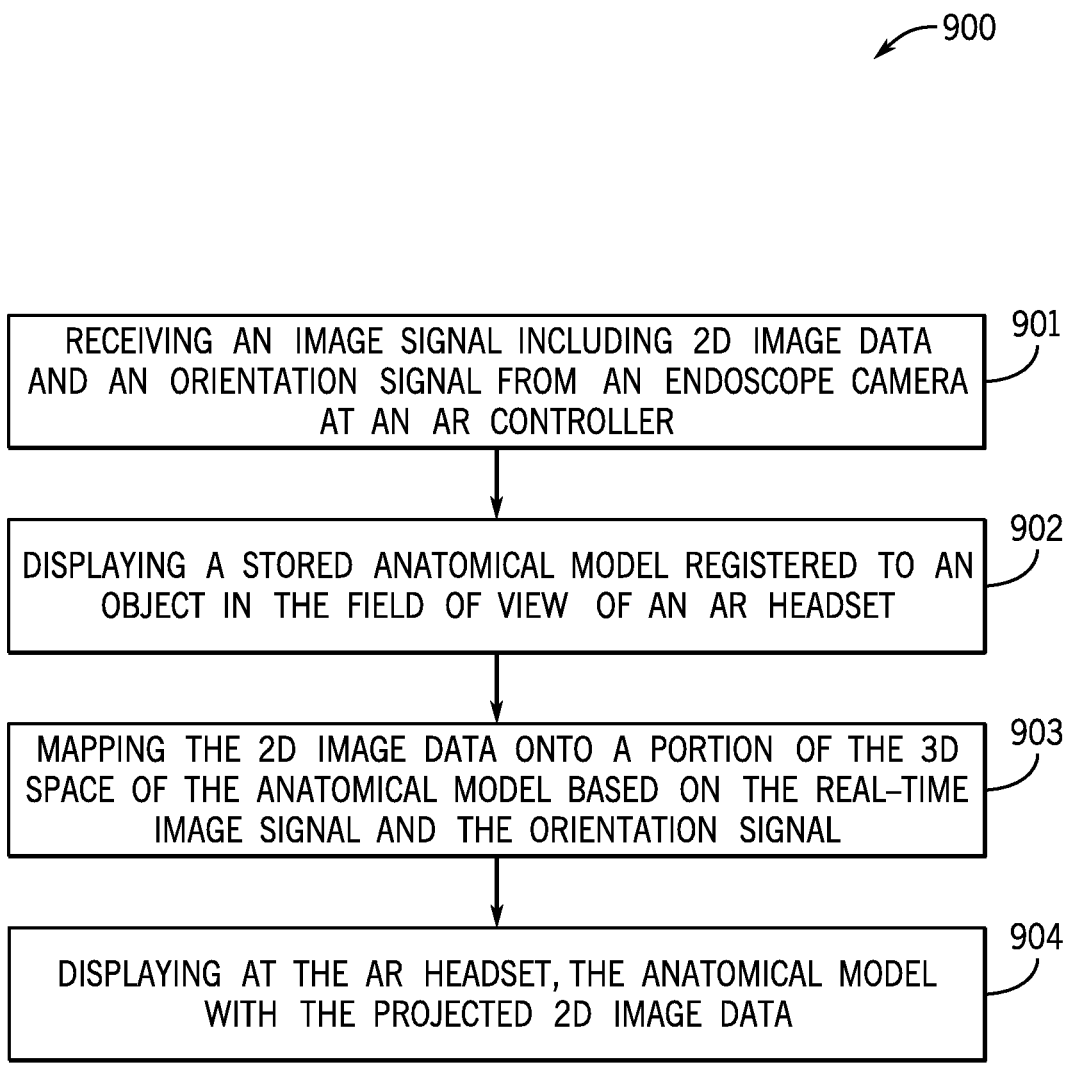
FIG. 9 is a flowchart of a method of providing an augmented reality view of a patient during a procedure with an endoscope, according to an embodiment of the disclosure.

FIG. 9 is a flowchart depicting a method 900 for incorporating live image data in an augmented reality view of a patient during a procedure with an endoscope, according to an embodiment of the disclosure. The method includes receiving, at an AR controller, an orientation signal and an image signal from an endoscope, at 901. The orientation signal includes position, orientation, and/or movement data from the orientation sensor of the endoscope, and the image signal includes 2D image data from the camera of the endoscope. The method also includes displaying virtual objects overlaid onto a real-world field of view of an AR headset in communication with the AR controller, at 902, including displaying a stored three-dimensional anatomical model registered to an object in the field of view of the AR headset. The method also includes mapping the 2D image data from the camera onto a portion of the 3D anatomical model based on the real-time image signal and the orientation signal, at 903 and displaying the anatomical model with the projected 2D image data mapped into the 3D space of the anatomical model, at 904.

The processors (such as 770, 780, 790) may be a chip, a processing chip, a processing board, a chipset, a microprocessor, or similar devices. The controllers 714, 718 and the viewer 716 may also include a user input (touch screen, buttons, switches). The controllers 714, 718 may also include a power source (e.g., an integral or removable battery) that provides power to one or more components of the controller, endoscope, or viewer as well as communications circuitry to facilitate wired or wireless communication with other devices. In one embodiment, the communications circuitry may include a transceiver that facilitates handshake communications with remote medical devices or full-screen monitors. The communications circuitry may provide the received images to additional monitors in real time.

The processor may include one or more application specific integrated circuits (ASICs), one or more general purpose processors, one or more controllers, FPGA, GPU, TPU, one or more programmable circuits, or any combination thereof. For example, the processor may also include or refer to control circuitry for the display screen. The memory may include volatile memory, such as random access memory (RAM), and/or non-volatile memory, such as read-only memory (ROM). The image data may be stored in the memory, and/or may be directly provided to the processor. Further, the image data for each patient procedure may be stored and collected for later review. The memory may include stored instructions, code, logic, and/or algorithms that may be read and executed by the processor to perform the techniques disclosed herein.

While the present techniques are discussed in the context of endotracheal intubation, it should be understood that the disclosed techniques may also be useful in other types of airway management or clinical procedures. For example, the disclosed techniques may be used in conjunction with placement of other devices within the airway, secretion removal from an airway, arthroscopic surgery, bronchial visualization past the vocal cords (bronchoscopy), tube exchange, lung biopsy, nasal or nasotracheal intubation, etc. In certain embodiments, the disclosed visualization instruments may be used for visualization of anatomy (such as the pharynx, larynx, trachea, bronchial tubes, stomach, esophagus, upper and lower airway, ear-nose-throat, vocal cords), or biopsy of tumors, masses or tissues. The disclosed visualization instruments may also be used for or in conjunction with suctioning, drug delivery, ablation, or other treatments of visualized tissue and may also be used in conjunction with endoscopes, bougies, introducers, scopes, or probes. Further, the disclosed techniques may also be applied to navigation and/or patient visualization using other clinical techniques and/or instruments, such as patient catheterization techniques. By way of example, contemplated techniques include cystoscopy, cardiac catheterization, catheter ablation, catheter drug delivery, or catheter-based minimally invasive surgery.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims.

What is claimed is:

1. A computer-implemented method for generating an augmented reality display over a field of view, comprising:
   receiving, at a controller, a position signal from an endoscope, the position signal comprising position, orientation, or movement data of a steerable distal end of the endoscope;
   receiving, at the controller, sensor signals from one or more sensors of the endoscope, the sensor signals comprising real-time data including a two-dimensional (2D) camera image associated with the current position of the endoscope;
   rendering, at the controller, virtual objects comprising:
      a three-dimensional anatomical model registered to a real object in the field of view;
      an endoscope marker positioned within the anatomical model at the current position of the endoscope; and
      a three-dimensional image portion, based on the 2D camera image, mapped onto the three-dimensional anatomical model in front of the endoscope marker; and
   displaying the virtual objects through a head-mounted viewer.

2. The method of claim 1, further comprising updating the virtual objects according to the position signal and the 2D camera image from the one or more sensors of the endoscope.

3. The method of claim 2, wherein updating the virtual objects comprises moving the endoscope marker and the three-dimensional image portion within the anatomical model along with movement of the endoscope.

4. The method of claim 1, wherein the endoscope marker comprises a tubular body and a camera frustum.

5. The method of claim 1, wherein the virtual objects further include a floating window comprising the 2D camera image.

6. The method of claim 1, wherein the three-dimensional image portion includes texturing of the three-dimensional anatomical model with features identified in the 2D camera image.

7. The method of claim 6, wherein the features identified in the 2D camera image include one of a tracheal ring or a tool.

8. The method of claim 7, wherein the features identified in the 2D camera image further include an anatomy landmark.

9. The method of claim 1, wherein the three-dimensional image portion is mapped onto a region of the three-dimensional anatomical model that correlates to a real world field of view of an endoscope camera capturing the 2D camera image.

10. The method of claim 1, wherein the one or more sensors comprise an ultrasound transducer or a time of flight sensor.

11. The method of claim 1, further comprising:
   identifying, at the controller, a deviation between the real-time data and the anatomical model; and
   generating a notification, at the head-mounted display, of the deviation.

* * * * *